United States Patent [19]
Salmi et al.

[11] Patent Number: 5,616,468
[45] Date of Patent: Apr. 1, 1997

[54] COMPOSITIONS AND DIAGNOSTIC METHODS USING MONOCLONAL ANTIBODIES AGAINST CD44V6

[76] Inventors: Marko Salmi, Vähä-Hämeenkatu 12 aB 30, 20500 Turku; Sirpa Jalkanen, Rauvolantie 112, 20760 Piispanristi, both of Finland

[21] Appl. No.: 453,378

[22] Filed: May 30, 1995

Related U.S. Application Data

[63] Continuation of Ser. No. 78,063, Jun. 18, 1993, abandoned.

[51] Int. Cl.$^6$ ................................................. G01N 33/574
[52] U.S. Cl. .................... 435/7.23; 435/7.24; 435/7.9; 530/388.8; 530/388.85; 436/63; 436/813
[58] Field of Search .................................. 435/7.23, 7.24, 435/7.9; 530/388.8, 388.85; 436/63, 813

[56] References Cited

FOREIGN PATENT DOCUMENTS 538754   4/1993   European Pat. Off. .
WO91/17248  11/1991  WIPO .

OTHER PUBLICATIONS

Arch, R. et al., Participation in Normal Immune Responses of a Metastasis–Inducing Splice Variant of CD44, *Science* 257:682–685 (1992).
Aruffo, A. et al., CD44 Is the Principal Cell Surface Receptor for Hyaluronate, *Cell* 61:1303–1313 (1990).
Belitsos, P.C. et al., Homotypic Cell Aggregation Induced By Anti–CD44(Pgp–1) Monoclonal Antibodies And Related To CD44(Pgp–1) Expression, *Journal of Immunology* 144:1661–1670 (1990).
Brown, T.A. et al., Human Keratinocytes Express a New CD44 Core Protein (CD44E) as a Heparan–Sulfate Intrinsic Membrane Proteoglycan with Additional Exons, *Journal of Cell Biology* 113:207–221 (1991).
Culty, M. et al., The Hyaluronate Receptor is a Member of the CD44 (H–CAM) Family of Cell Surface Glycoproteins, *Journal of Cell Biology* 111:2765–2774 (1990).
Dougherty, G.J. et al., Molecular Cloning of CD44R1 and CD44R2, Two Novel Isoforms of the Human CD44 Lymphocyte "Homing" Receptor Expressed by Hemopoietic Cells, *J. Exp. Med.* 174:1–5 (1991).
Gallatin, W.M. et al., Structural homolgy between lymphocyte receptors for high endothelium and class III extracellular matrix receptor, *Proc. Natl. Acad. Sci. USA* 86:4654–4658 (1989).
Goldstein, L.A. et al., A Human Lymphocyte Homing Receptor, the Hermes Antigen, Is Related to Cartilage Proteoglycan Core and Link Proteins, *Cell* 56:1063–1072 (1989).
Günthert, U. et al., A New Variant of Glycoprotein CD44 Confers Metastatic Potential to Rat Carcinoma Cells, *Cell* 65:13–24 (1991).
Haynes, B.F. et al., The Transmembrane Hyaluronate Receptor (CD44): Multiple Functions, Multiple Forms, *Cancer Cells* 3(9):349–350 (1991).
Haynes, B.F. et al., CD44 – A molecule involved in leukocyte adherence and T–cell activation, *Immunology Today* 10(12):423–428 (1989).
Hofmann, M. et al., CD44 Splice Variants Confer Metastatic Behavior in Rats: Homologous Sequences Are Expressed in Human Tumor Cell Lines, *Cancer Research* 51:5292–5297 (1991).
Horst, E. et al., Adhesion Molecules in the Prognosis of Diffuse Large–Cell Lymphoma: Expression of a Lymphocyte Homing Receptor (CD44), LFA–1, (CD11a/18), and ICAM–1 (CD54), *Leukemia* 4:595–599 (1990).
Jackson, D.G. et al., Multiple Variants of the Human Lymphocyte Homing Receptor CD44 Generated by Insertions at a Single Site in the Extracellular Domain, *Journal of Biol. Chem.* 267:4732–4739 (1992).
Jalkanen, S. et al., Biochemical Properties of Glycoproteins Involved In Lymphocyte Recognition of High Endothelial Venules in Man, *Journal of Inunology* 141:1615–1623 (1988).
Jalkanen, S. et al., Lymphocyte Homing and Clinical Behavior of Non–Hodgkin's Lymphoma, *J. Clin. Invest* 87:1835–1840 (1991).
Jalkanen, S. et al., Lymphocyte CD44 Binds the COOH–terminal Heparin–binding Domain of Fibronectin, *Journal of Cell Biology* 116(3):817–825 (1992).

(List continued on next page.)

*Primary Examiner*—Toni R. Scheiner
*Attorney, Agent, or Firm*—Sterne, Kessler, Goldstein & Fox, p.l.l.c.

[57] ABSTRACT

CD44 is a family of glycoproteins involved in cell-cell and cell-matrix interactions. In addition to the major 90 kD form present on most hematopoietic cells, larger forms are found on keratinocytes and carcinoma cell lines. These bigger isoforms of CD44 arise by alternative splicing that results in insertion of one or more of the "variant" exons into the extracellular part of the 90 kD constant form of the molecule. Antibodies were raised against a synthetic peptide containing a sequence encoded by the human exon 6A mAb thus obtained (designated Var3.1) strongly reacted with the plasma membranes of squamous cells in upper layers of skin and tonsil surface epithelia. Weaker staining was seen in germinal centers, vascular endothelia and enterocytes. CD44v6 was absent from tissue leukocytes and connective tissue components. In comparison, Hermes-3 epitope (on the constant part) containing forms of CD44 were preferentially localized in basal layers of epithelia, present on the surface of most leukocytes and connective tissue cells, and undetectable on the luminal surface of high endothelial venules. In benign neoplasms, epithelial cells stained with mAb Var3.1 like in normal tissues. In contrast, immunostaining of 30 squamous carcinoma specimens (both primary and metastatic lesions) revealed that malignant transformation resulted in down-regulation or disappearance of Var3.1 epitope, but in majority of cases, not in diminished expression of the Hermes-3 epitope. An examination of serum samples from normal individuals and from patients with inflammatory diseases indicated that CD44v6 was increased in samples from patients with rheumatoid arthritis or inflammatory bowel disease.

14 Claims, 13 Drawing Sheets

OTHER PUBLICATIONS

Jalkanen, S. et al., Lymphocyte Recognition of High Endothelium: Antibodies to Distinct Epitopes of an 85–95–kD Glycoprotein Antigen Differentially Inhibit Lymphocyte Binding to Lymph Node, Mucosal, or Synovial Endothelial Cells, *Journal of Cell Biology* 105:983–990 (1987).

Jalkanen, S. et al., A lymphoid cell surface glycoprotein involved in endothelial cell recognition and lymphocyte homing in man, *Eur. J. Immunol.* 16:1195–1202 (1986).

Matsumura, Y. et al., Significance of CD44 gene products for cancer diagnosis and disease evaluation, *The Lancet* 340:1053–1058 (1992).

Miyake, K. et al., Monoclonal Antibodies To Pgp–1/CD44 Block Lympho–Hemopoiesis In Long–Term Bone Marrow Cultures, *J. Exp. Med.* 171:477–488 (1990).

Omary, M.B. et al., Structural heterogeneity of human Pgp–1 and its relationship with p85, *Immunogenetics* 27:460–464 (1988).

Oppenheimer–Marks, N. et al., Human T Lymphocyte Adhesion To Endothelial Cells And Transendothelial Migration, *Journal of Immunology* 145:140–148 (1990).

Picker, L. et al., Monoclonal Antibodies to Human Lymphocyte Homing Receptors Define a Novel Class of Adhesion Molecules on Diverse Cell Types, *Journal of Cell Biology* 109:927–937 (1989).

Picker, L.P. et al., Monoclonal Antibodies Against The CD44 [In(Lu)–Related p80], And Pgp–1 Antigens In Man Recognize The Hermes Class of Lymphocyte Homing Receptors, *J. Immunol.* 142:2046–2051 (1989).

Stamenkovic, I. et al., A Lymphocyte Molecule Implicated in Lymph Node Homing Is a Member of the Cartilage Link Protein Family, *Cell* 56:1057–1062 (1989).

Stamenkovic, I. et al., The hematopoietic and epithelial forms of CD44 are distinct polypeptides with different adhesion potenitals for hyaluronate–bearing cells, *The EMBO Journal* 10:343–348 (1991).

Sy, M.S. et al., Distinct Effects of Two CD44 Isoforms on Tumor Growth In Vivo, *J. Exp. Med.* 174:859–866 (1991).

Webb, D.S. et al., LFA–3, CD44, and CD45: Physiologic Triggers of Human Monocyte TNF and IL–1 Release, *Science* 249:1295–1297 (1990).

English Translation of PCT application WO 91/17248, submitted herewith as document AL1.

Koopman et al., *J. Exp. Med.*, vol. 177, pp. 897–904, Apr. 1993.

Heider et al., *J. Cell Biol.*, vol. 120, No. 1, pp. 227–233, Jan. 1993.

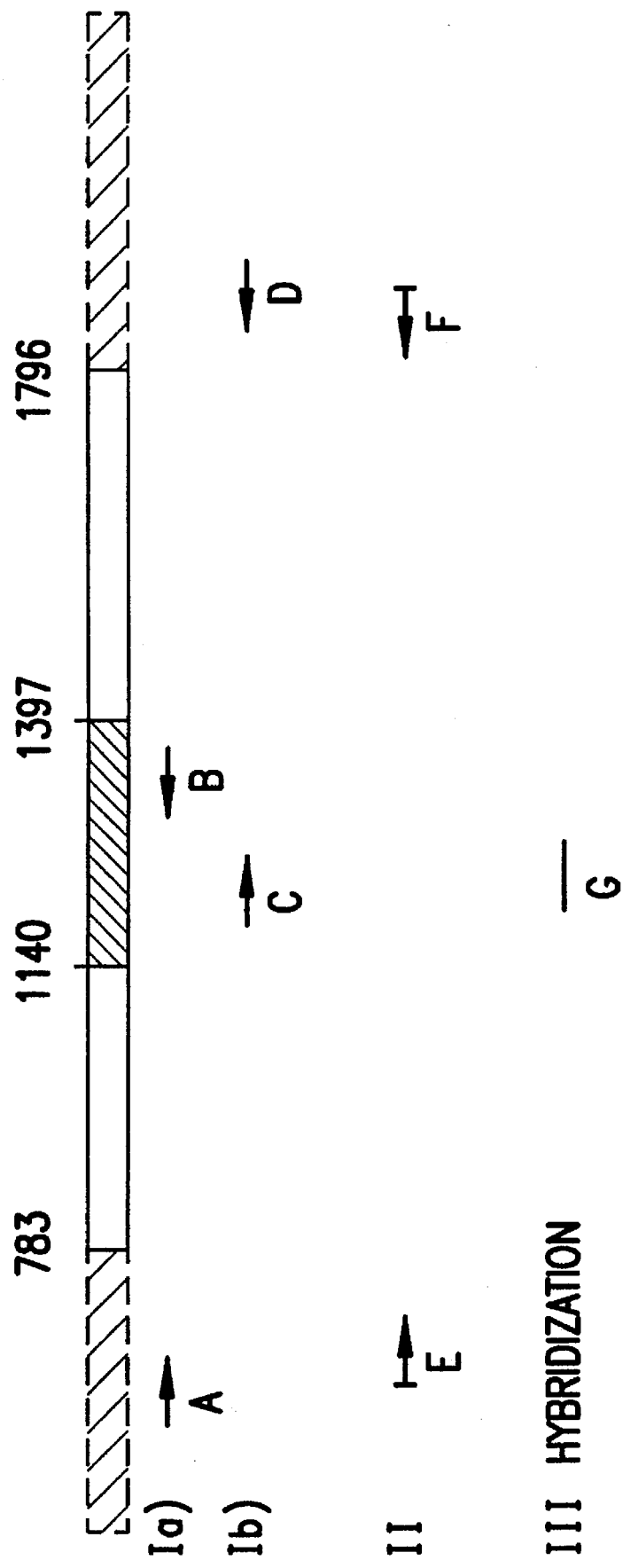

```
pos. 1140 -TC CAG GCA ACT CCT AGT ACA ACG GAA GAA ACA GCT ACC
CAG AAG GAA CAG TGG TTT GGC AAC AGA AGA TGG CAT GAG GGA TAT CGC CAA ACA
CCC AGA GAA GAC TCC CAT TCG ACA ACA GGG ACA GCT G- pos. 1267
```

FIG.11

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 17 amino acids
        ( B ) TYPE: amino acid
        ( D ) TOPOLOGY: linear ( x i ) SEQUENCE DESCRIPTION: SEQ ID NO:1:

```
Ser  Thr  Thr  Glu  Glu  Thr  Ala  Thr  Gln  Lys  Glu  Gln  Trp  Phe  Gly  Asn
1                 5                             10                           15

Cys
```

( 2 ) INFORMATION FOR SEQ ID NO:2:

( i ) SEQUENCE CHARACTERISTICS:
        ( A ) LENGTH: 24 amino acids
        ( B ) TYPE: amino acid
        ( D ) TOPOLOGY: linear ( x i ) SEQUENCE DESCRIPTION: SEQ ID NO:2:

```
Asp  Glu  Leu  Pro  Gln  Val  Thr  Leu  Pro  His  Pro  Asn  Leu  His  Gly  Pro
1                 5                             10                           15

Glu  Ile  Leu  Asp  Val  Pro  Ser  Thr
                 20
```

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: both
        ( D ) TOPOLOGY: both ( x i ) SEQUENCE DESCRIPTION: SEQ ID NO:3:

```
CAATTACCAT  AACTATTGTT  AACCG                                                 25
```

( 2 ) INFORMATION FOR SEQ ID NO:4:

( i ) SEQUENCE CHARACTERISTICS:
        ( A ) LENGTH: 21 base pairs
        ( B ) TYPE: nucleic acid ( C ) STRANDEDNESS: both
( D ) TOPOLOGY: both ( x i ) SEQUENCE DESCRIPTION: SEQ ID NO:4:

AATCAGTCCA GGAACTGTCC T                                                    21

( 2 ) INFORMATION FOR SEQ ID NO:5:

( i ) SEQUENCE CHARACTERISTICS:
( A ) LENGTH: 20 base pairs
( B ) TYPE: nucleic acid
( C ) STRANDEDNESS: both
( D ) TOPOLOGY: both ( x i ) SEQUENCE DESCRIPTION: SEQ ID NO:5:

GGCAACAGAT GGCATGAGGG                                                      20

( 2 ) INFORMATION FOR SEQ ID NO:6:

( i ) SEQUENCE CHARACTERISTICS:
( A ) LENGTH: 25 base pairs
( B ) TYPE: nucleic acid
( C ) STRANDEDNESS: both
( D ) TOPOLOGY: both ( x i ) SEQUENCE DESCRIPTION: SEQ ID NO:6:

AGTGGTATGG GACCCCCAC TGGGG                                                 25

( 2 ) INFORMATION FOR SEQ ID NO:7:

( i ) SEQUENCE CHARACTERISTICS:
( A ) LENGTH: 28 base pairs
( B ) TYPE: nucleic acid
( C ) STRANDEDNESS: both
( D ) TOPOLOGY: both ( x i ) SEQUENCE DESCRIPTION: SEQ ID NO:7:

ATAGGATCCA ACCGTGATGG CACCCGCT                                             28

( 2 ) INFORMATION FOR SEQ ID NO:8:

( i ) SEQUENCE CHARACTERISTICS:
( A ) LENGTH: 27 base pairs
( B ) TYPE: nucleic acid
( C ) STRANDEDNESS: both
( D ) TOPOLOGY: both ( x i ) SEQUENCE DESCRIPTION: SEQ ID NO:8:

TATGAATTCG GAATGTGTCT TGGTCTC                                              27

( 2 ) INFORMATION FOR SEQ ID NO:9:

( i ) SEQUENCE CHARACTERISTICS:
( A ) LENGTH: 20 base pairs
( B ) TYPE: nucleic acid
( C ) STRANDEDNESS: both
( D ) TOPOLOGY: both ( x i ) SEQUENCE DESCRIPTION: SEQ ID NO:9:

GCTGTCCCTG TTGTCGAATG                                                      20

( 2 ) INFORMATION FOR SEQ ID NO:10:

( i ) SEQUENCE CHARACTERISTICS:
( A ) LENGTH: 16 amino acids
( B ) TYPE: amino acid
( D ) TOPOLOGY: linear ( x i ) SEQUENCE DESCRIPTION: SEQ ID NO:10:

```
Ser Thr Thr Glu Glu Thr Ala Thr Gln Lys Glu Gln Trp Phe Gly Asn
1               5                   10                  15
```

( 2 ) INFORMATION FOR SEQ ID NO:11:

( i ) SEQUENCE CHARACTERISTICS:
      ( A ) LENGTH: 129 base pairs
      ( B ) TYPE: nucleic acid
      ( C ) STRANDEDNESS: both
      ( D ) TOPOLOGY: both ( x i ) SEQUENCE DESCRIPTION: SEQ ID NO:11:

```
TCCAGGCAAC TCCTAGTAGT ACAACGGAAG AAACAGCTAC CCAGAAGGAA CAGTGGTTTG        60

GCAACAGATG GCATGAGGGA TATCGCCAAA CACCCAGAGA AGACTCCCAT TCGACAACAG       120

GGACAGCTG                                                               129
```

COMPOSITIONS AND DIAGNOSTIC METHODS USING MONOCLONAL ANTIBODIES AGAINST CD44V6

This application is a continuation of application Ser. No. 08/078,063, filed Jun. 18, 1993 which is abandoned.

BACKGROUND OF THE INVENTION

1. Field of the Invention

The field of invention relates to immunological reagents and methods for detecting the expression of specific antigens. Specifically, the invention relates to a monoclonal antibody which detects a variant of the membrane glycoprotein CD44. The immunological reagent of the present invention is useful as a diagnostic tool for detecting malignant transformation, assessing metastatic potential and for diagnosing inflammatory diseases.

2. Description of the Background Art

Cell-cell and cell-matrix interactions are of fundamental importance to multicellular organisms in controlling growth, differentiation and in the migration of cells. CD44 is one of the molecules known to be involved in these adhesion-dependent processes. In man, CD44 was independently discovered by several groups using antibodies against molecules referred to as "brain-granulocyte-T lymphocyte antigen"; "human medullary thymocyte antigen"; "Lutheran inhibitor related antigen"; "p85"; "phagocytic glycoprotein-1"; "Hermes-antigen"; "extracellular matrix receptor type III"; and "hyaluronate receptor" (Carter, W. G. et al., *J. Biol. Chem.* 263:4193–4201 (1988); Dalchau, R. et al., *Eur. J. Immunol.* 10:745–749 (1980); Haynes, B. F. et al., *J. Immunol.* 131:1195–1200 (1983); Isacke, C. M. et al., Immunogenetics 23:326–332 (1986); Jalkanen, S. et al., *Eur. J. Immunol.* 16:1195–1202 (1986); Letarte M. et al., *Mol. Immunol* 22:113–124 (1985); Telen, M. J. et al., *J. Clin. Invest.* 71:878–1886 (1983); Underhill, C. B. et al., *J. Biol. Chem.* 262:1142–13146 (1987)). Subsequently, these antibodies were shown to identify the same molecule, CD44 (Culty, M. et al., *J. Cell Biol.* 111:2765–2774 (1990); Gallatin, W. M. et al., *Proc. Natl. Acad. Sci. USA* 86:4654–4658 (1989); Omary, M. B. et al., *Immunogenetics* 27:460–464 (1988); Picker, L. J. et al., *J. Immunol.* 142:2046–051 (1989)).

CD44 is a multifunctional glycoprotein involved in: lymphocyte-endothelial cell interactions; adhesion of cells to extracellular matrix proteins; lymphohematopoiesis; homotypic adhesion; T cell activation and adherence; cytokine release; metastasis and the lateral movement of cells (Haynes, B. F. et at., *Cancer Cells* 3:347–350 (1991); Haynes, B. F. et at., *Immunol. Today* 10:423–428 (1989); Jalkanen, S. T. et al., *J. Cell. Biol.* 105:983–990 (1987); Jalkanen, S. et al., *Eur. J. Immunol.* 16:1195–1202 (1986); Oppenheimer-Marks, N. et al., *J. Immunol.* 145:140–148 (1990); Picker, L. J. et al., *J. Cell. Biol.* 109:927–938 (1989); Aruffo, A. et al., *Cell* 61:1303–1313 (1990); Carter, W. G. et al., *J. Biol. Chem.* 263:4193–4201 (1988); Jalkanen, S. et al., *J. Cell. Biol.* 116:817–825 (1992); Miyake, K. et al., *J. Exp. Med.* 172:69–75 (1990); Underhill, C. B. et al., *J. Biol. Chem.* 262:1142–13146 (1987)); Miyake, K. et al., *J. Exp. Med.* 171:477–488 (1990); Belitsos, P. C. et al., *J. Immunol.* 144:1661–1670 (1990); St. John, T. et al., *Cell* 60:45–52 (1990); Arch, R. et al., *Science* 257:682–685 (1992); Denning, S. M. et al., *J. Immunol.* 144:7–15 (1990); Hale, L. P. et al., *J. Immunol.* 143:3944–3948 (1989); Huet, S. et al., *J. Immunol.* 143:798–801 (1989); Kalomiris, E. L. et al., *J. Cell Biol.* 106:319–327 (1988); Rothman, B. L. et al., *J. Immunol.* 147:2493–2499 (1991); Seth, A. et at., *Proc. Natl. Acad. Sci. USA* 88:7877–7881 (1991); Shimizu, Y. et al., *J. Immunol.* 143:2457–2463 (1989); Webb, D. S. A. et al., *Science* 249:1295–1297 (1990); Jacobson, K. et al., *J. Cell Biol.* 99:1613–1623 (1984)).

CD44 is widely distributed among several hematopoietic and nonhematopoietic cells including all subsets of leukocytes, erythrocytes, many types of epithelial cells, fibroblasts, smooth muscle cells and glial cells of the central nervous system (Carter, W. G. et al., *J. Biol. Chem.* 263:4193–4201 (1988); Dalchau, R. et al., *Eur. J. Immunol.* 10:745–749 (1980); Haynes, B. F. etal., *J. Immunol.* 131:1195–1200 (1983); Isacke, C. M. etal., *Immunogenetics* 23:326–332 (1986); Jalkanen, S. et al., *Eur. J. Immunol.* 16:1195–1202 (1986); Letarte M. et al., *Mol. Immunol* 22:113–124 (1985); Lucas, M. G. et al., *Blood* 735:596–600 (1989); Picker, L. J. et al., *J. Cell. Biol.* 109:927–938 (1989); Telen, M. J. et al., *J. Clin. Invest.* 71:878–1886 (1983)). Most hematopoietic cells, fibroblasts and glial cells predominantly express a 90 kD form of CD44. Lymphocytes also express a 180 kD form which represents a chondroitin sulfate modification of the 90 kD backbone (Jalkanen, S. et al., *J. Immunol.* 141: 16 15–1623 (1988)). In contrast, the CD44 antigen in epithelial cell lines is considerably larger (140–160 kD), and still larger forms, up to 230 kD have been described (Brown, T. A. et al., *J. Cell Biol.* 113:207–221 (1991); Omary, M. B. et al., *Immunogenetics* 27:460–464 (1988); Picker, L. J. et al., *J. Cell. Biol.* 109:927–938 (1989)).

Recently, the molecular basis underlying the biochemically distinct forms of CD44 has been resolved. Molecular cloning of human CD44 from lymphoid lines revealed a gene which encodes an integral membrane glycoprotein having an N-terminal extracellular region, a short hydrophobic transmembrane region and a cytoplasmic tail (Goldstein, A. L. et al., *Cell* 56:1063–1072 (1989); Stamenkovic, I. et al., *Cell* 56:1057–1062 (1989)). Subsequently, the structure of an epithelial form of 150 kD from keratinocytes and carcinoma cell lines was analyzed (Brown, T. A. et al., *J. Cell Biol.* 113:207–221 (1991); Stamenkovic, I. et al., *EMBO J.* 10:343–348 (1991)). The epithelial form was found to contain an additional stretch of 132 amino acids inserted in the membrane proximal part of the peptide backbone common to both the lymphocyte and epithelial forms. Forms containing the same 132 amino acid sequence or a shorter part of it were also found in hematopoietic cells (Dougherty, G. J. et al., *J. Exp. Med.* 174:1–5 (1991)).

In both the rat, and in man, five distinct amino acid sequence elements (or "domains") have been identified which may be found expressed as part of the 90 kD core CD44 protein (Günthert, U. et al., *Cell* 65:13–24 (1991); Hoffman, M. et al., *Cancer Res.* 51:5292–5297 (1991); Jackson, D. G. et al., *J. Biol. Chem.* 26:4732–4739 (1992); Kugelman, L. et al., *J. Invest. Dermatol.* 99:381–385 (1992)). These domains are encoded by at least ten distinct exons named v1–v10 (Arch, R. et al., *Science* 257:682–685 (1992)). CD44 molecules containing one or more of these exons within the common protein backbone are designated as variant forms to distinguish them from the major 90 kD lymphocyte form (standard). Herein, the term exon v6 will be used for nucleotides 1140–1267 of the largest known form of human CD44 (Hoffman, M. et al., *Cancer Res.* 51:5292–5297 (1991)).

CD44 isoforms play important and distinct roles in tumor invasiveness and metastasis. The standard 90 kD lymphocyte form apparently contributes to the metastatic capacity of non-Hodgkin lymphoma cells in man (Horst, E. et al., Leukemia 4:595-599 (1990); Jalkanen, S. et al., J. Can. Invest. 87:1835-1840 (1991)). The lymphocyte form, but not the 150 kD epithelial form (containing exons 8-10 according to the exon nomenclature), also enhances local tumor formation and the metastatic potential of transfected lymphoma cells in a nude mouse model (Sy, M. S. et al., J. Exp. Med. 174:859-866 (1991)). Expression of the epithelial form is increased in carcinoma cell lines, which may suggest a role in tissue invasiveness (Stamenkovic, I. et al., Cell 56:1057-1062 (1989)). Finally, using a monoclonal antibody which recognizes rat variant CD44, Herrlich reported a direct correlation between CD44 expression and the metastasis of adenocarcinoma cells (PCT International Appl. No. WO 91/17248; see also, Günthert, U. et al., Cell 65:13-24 (1991)).

In man, analysis of the expression pattern of the variant forms of CD44 has been limited to studies on the CD44 variant mRNAs present in cells (Hoffman, M. et al., Cancer Res. 51:5292-5297 (1991)). This is because, prior to the present invention, there were no monoclonal antibodies available capable of distinguishing between the standard and variant CD44s in man. Studies which rely upon mRNA levels as an indicator of protein expression are inherently unreliable due to the fact that mRNAs may or may not be translated. As a result, prior to the present invention, it was not known what kind of tissue distribution the variant forms of CD44 exhibited in man. Moreover, it was not clear, how expression of different isoforms was regulated during normal cell differentiation or what kind of changes in expression might accompany pathological conditions such as malignant transformation, metastasis or inflammatory diseases.

The inventors have produced monoclonal antibodies against exon v6 of the human variant CD44. Distribution of exon v6 containing forms of CD44 (CD44v6) in normal tissues and tumors was determined, and compared to that of the forms recognized by mAb Hermes-3, an antibody recognizing the 90 kD CD44 core protein. The results indicate that antibodies which specifically to recognize the amino acid sequence encoded by exon v6 can be used in the detection of malignant transformation and in assessing the metastatic potential of transformed cells. Other results indicate that such antibodies can be used to detect the presence of inflammatory diseases in people.

BRIEF DESCRIPTION OF THE FIGURES

FIGS. 2A, 2B and 2C: MAb Var3.1 recognizes recombinant proteins carrying exon v6. 2A) Schematic representation of the PCR strategy used to amplify CD44v6 from HaCat cells (see text for details). Box represents the variant part of CD44 and exons v6 and v7 are highlighted as a darkened area.

Figure 1:
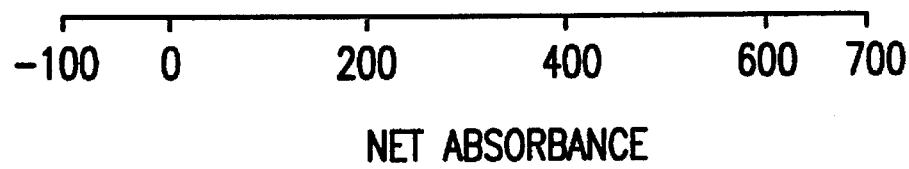
FIG. 1. MAb Var3.1 is specific for human exon v6 of CD44. Binding of mAbs Var3.1, Hermes-3 and 3G6 (negative control) to v6 specific peptide (STTEETATQKEQW-FGN-C [SEQ ID NO: 1]) and to an irrelevant peptide (DELPQVTLPHPNLHGPEILDVPST [SEQ ID NO: 2]) was determined. Results are presented as net absorbances (mean±SD) from triplicate samples of two independent ELISA experiments (net absorbance=absorbance to v6 specific peptide absorbance to control peptide).

Primers were as follows:

A: 5' CAATTACCATAACTATTGTTAACCG 3'[SEQ ID NO: 3],

B: 5' AATCAGTCCAGGAACTGTCCT 3'[SEQ ID NO: 4],

C: 5' GGCAACAGATGGCATGAGGG 3'[SEQ ID NO: 5],

D: 5' AGTGGTATGGGACCCCCCACTGGGG 3'[SEQ ID NO: 6],

E: 5' ATAGGATCCAACCGTGATGGCACCCGCT 3'[SEQ ID NO: 7],

F: 5' TATGAATTCGGAATGTGTCTTGGTCTC 3'[SEQ ID NO: 8],

Probe G: 5' GCTGTCCCTGTTGTCGAATG 3'[SEQ ID NO: 9]. Numbering of nucleotides is based on data presented in Refs. 1 and 19. 2B) Coomassie blue staining of the whole cell lysates of transformed bacteria after IPTG induction. Lane 1: cells transformed with pGEX-2T (arrowhead: the ~28 kD product of the parent vector); Lane 2: cells transformed with pGEX-2T-Var (arrow: the ~60 kD fusion protein containing v6.2C) Immunoblotting of the same lysates. Whole cell lysates of IPTG-induced bacteria transformed with pGEX-2T-Var (lanes 1 and 3), and with pGEX-2T (lanes 2 and 4) were stained with mAbs Var3.1 (lanes 1 and 2) and 3G6 (negative control, lanes 3 and 4). MAb Var3.1 stains the ~60 kD fusion protein (lane 1, arrow) but not the product of pGEX-2T (lane 2). Both mAbs non-specifically reacted with a ~38 kD molecule. MW=molecular weight standards in kD.

Figure 3:
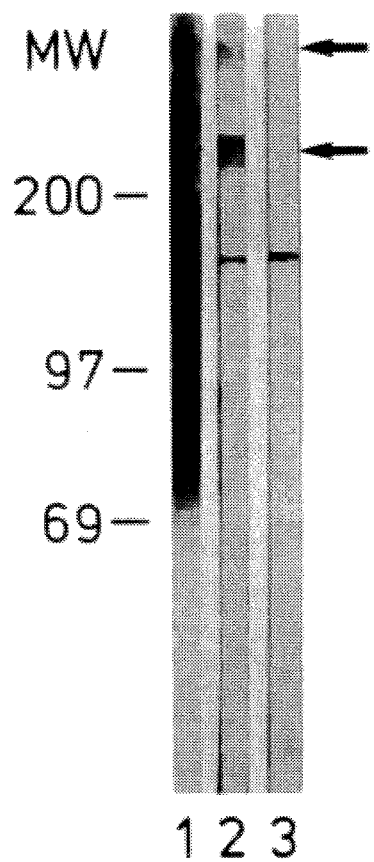

FIG. 3: Molecular weight of CD44v6. Hermes-3 reactive material was isolated from a leukopheresis sample using an affinity column, resolved in SDS-PAGE and blotted. Reactivity with mAbs Var3.1 and Hermes-3 was analyzed using immunoperoxidase method (see Materials and Methods). Lane 1, Hermes-3; lane 2, Var3.1; lane 3, 3G6 (negative control). Arrows point to the two major forms of CD44 recognized by mAb Var3.1. Molecular weight standards (kD) are indicated on the left.

FIGS. 4A, 4B, 4C, 4D and 4E show the tissue distribution of v6 and Hermes-3 epitope containing forms of CD44 in man. 4(A) A tonsil section stained with mAb Var3.1. Positive immunoperoxidase reaction is seen in the squamous cells of surface epithelium. Note the predominant staining in mid and upper layers. Lymphocytes are negative. 4(B) Higher magnification of tonsil epithelium stained with mAb Var3.1. 4(C) Expression of CD44v6 is heterogeneous on high endothelial venules. Some high endothelial venules are brightly positive (black arrows), whereas others are negative or weakly positive (white arrow). 4(D) A parallel tonsil section stained with Hermes-3. This antibody also stains all the layers of surface epithelium, but the expression is most prominent in the basal layers. Lymphocytes in the lymphatic area are brightly positive. 4(E) Hermes-3 epitope is absent from high endothelial venules (arrowheads pointing to the luminal surface). e, surface epithelium; 1a lymphoid area. Scale bar, 15 μm.

FIG. 5(A and B): v6 is expressed on the surface of squamous epithelial cells. 5(A) The plasma membranes of the superficial cells in the stratified squamous epithelium of tonsil are darkly stained by mAb Var3.1. Note that the more superficial side (arrows) of cells is systematically more strongly stained. Peroxidase reaction. 5(B) With gold-labeled secondary antibody the gold particles are localized along the plasma membrane. Streptavidin-gold without contrasting, the white outline (arrows) is the plasma membrane.

FIG. 6(A–I): Expression of CD44v6 on blood lymphocytes. 6A–F) Fresh PBL (PERM -, left column) do not express CD44v6 on their surface, but are Hermes-3 bright. When the cells are permeabilized with 1% formaldehyde and acetone prior $I_o$ staining (PERM +, right column), many cells become CD44v6 positive. X-axis is relative fluorescence on a log scale; y-axis is cell number. 6G–I) In immunofluorescence microscopy permeabilized PBL show intracellular staining for CD44v6, which preferentially is localized in the periphery of cells. Top: mAb 3G6 (negative control); middle: mAb Var3.1; bottom: mAb Hermes-3. Scale bar, 10 μm.

Figure 7:
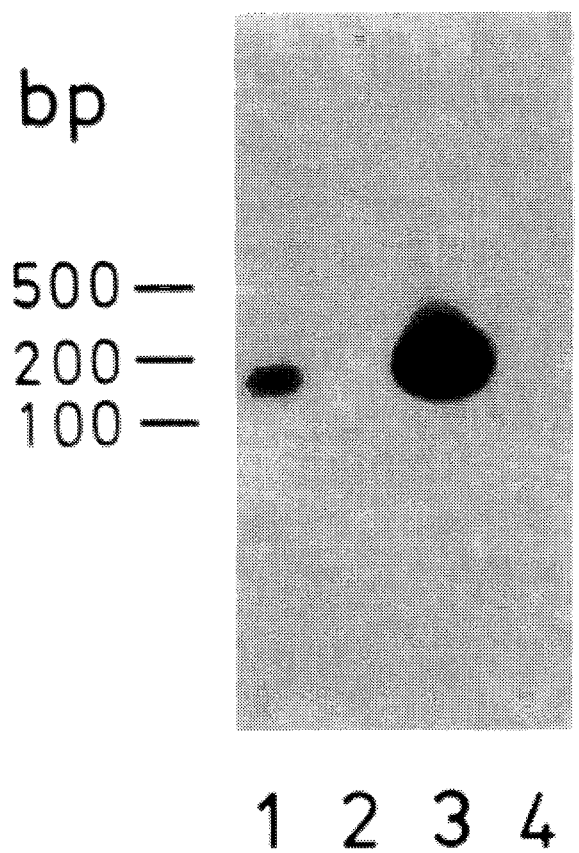
Figure 8A:
Figure 8B:
Figure 8C:
Figure 8D:
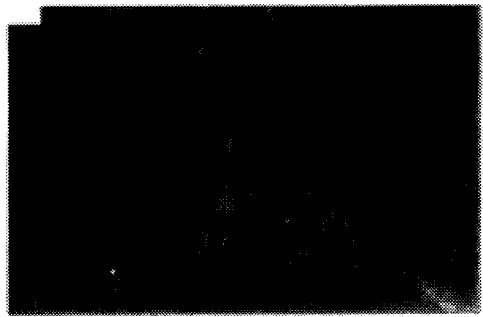
Figure 8E:
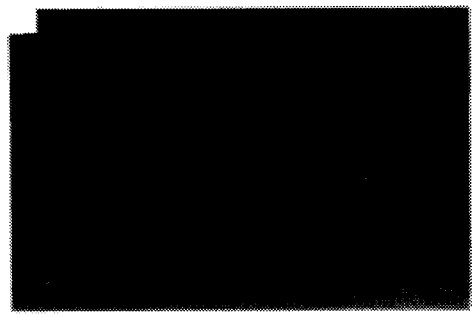
Figure 8F:
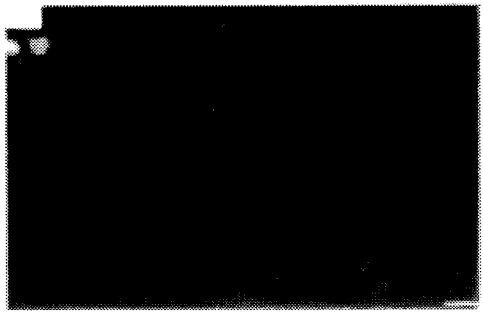
Figure 9A:
Figure 9B:
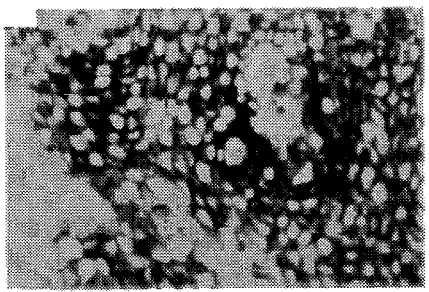
Figure 9C:
Figure 9D:
Figure 9E:
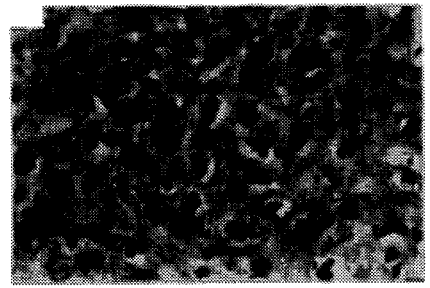
Figure 9F:
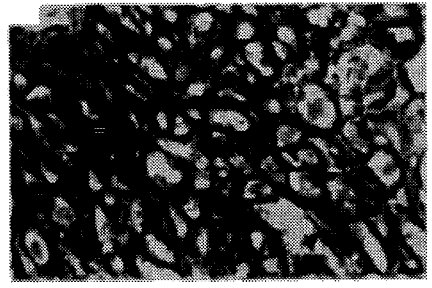
Figure 9G:
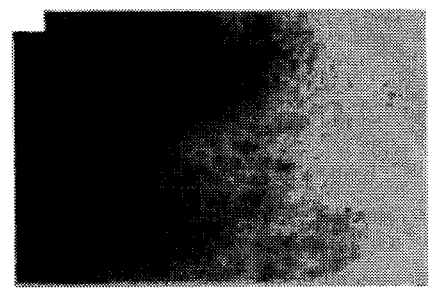
Figure 9H:
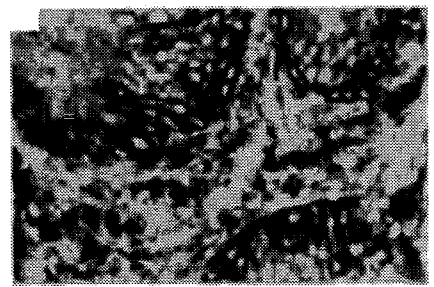

FIG. 7: v6-specific RNA is present in human PBL. RNA was isolated from PBL and HaCat cells, reverse transcribed to cDNA, PCR amplified with primers B and C (see FIG. 2A), separated in agarose gel, transferred onto nylon membrane and hybridized with a v6 specific probe (probe G, FIG. 2A). Lane 1: lymphocytes, lane 3 HaCaT cells. Lanes 2 (lymphocyte) and 4 (HaCaT) represent negative control reactions which were identical to those seen in lanes 1 and 3 with the exception that no reverse transcriptase was added into the cDNA synthesis reaction.

FIGS. 8A, 8B, 8C, 8D, 8E and 8F: CD44v6 is associated with the cytoskeleton. Fixed and permeabilized HaCaT cells were treated without (A–B) or with (C–F) 0.5% NP-40 prior to immunofluorescence staining with mAb Var3.1(A,C), Hermes-3 (B,D) and 3G6 (negative control, E,F). Significant amount of the Var3.1reactive material was resistant to NP-40 treatment, while Hermes-3 staining was greatly diminished after the treatment. Scale bar, 10 μm.

FIGS. 9A, 9B, 9C, 9D, 9E, 9F, 9G and 9H: Expression of CD44v6 in tumors. A benign cutaneous papilloma is positive with both mAb Var3.1(A) and mAb Hermes-3 (B). A squamocellular carcinoma of the skin displays greatly diminished expression 10 of CD44v6 (C), but remains brightly Hermes-3 positive (D). (E) Higher magnification from C. (F) Higher magnification from D. (G) Metastatic cells from squamocellular carcinoma are practically mAb Var3.1 negative, but (H) they still contain the Hermes-3 epitope. Scale bar, 15 μm.

Figure 10:
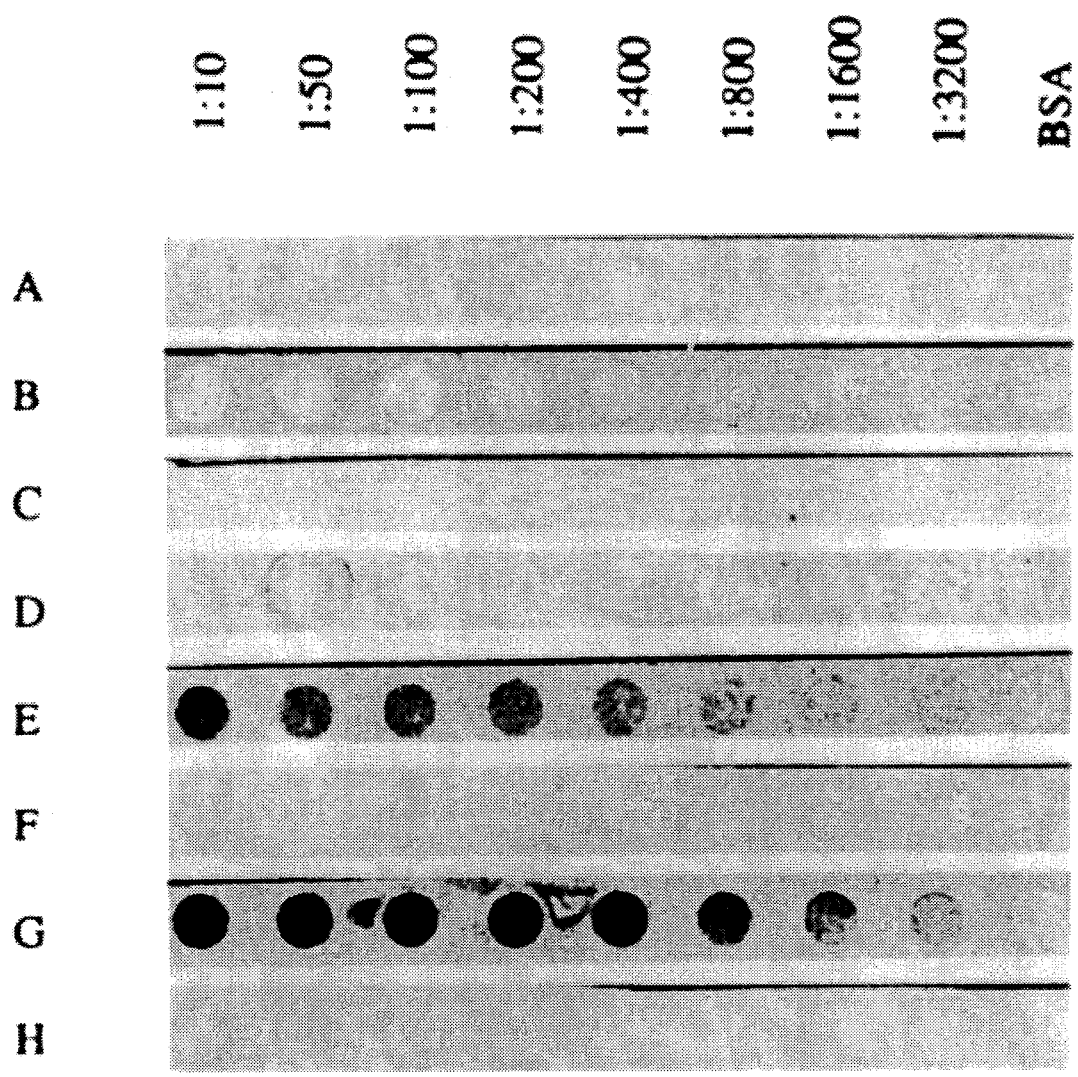

FIG. 10: Existence of CD44v6 in sera of patients suffering from chronic inflammation (rheumatoid arthritis). As representative examples, presence of CD44v6 and Hermes-3 epitope in serial dilutions (from 1:10 to 1:3200) of sera of two patients and of one normal subject are shown. Lanes A–C: normal subject; A: Hermes-3, B: Var3.1, C: 3G6, negative control. Lanes D–F: patient #1; D: Hermes-3, E: Var3.1, F:3G6 . Lanes G–H: patient #2; G: Var3.1, H:3G6. Hermes-3 staining was negative. BSA, control wells containing 50 μg BSA.

FIG. 11: Nucleotide sequence of exon v6 of CD44[SEQ ID NO: 11]. The nucleotides shown in bold type are those that encode amino acids that were used to prepare the synthetic peptide used for immunization. Nucleotide numbering is based on data reported in Stamenkovic et al., *Cell* 60:54 (1990) and Hofmann et al., *Cancer Res.* 51:5292 (1991).

SUMMARY OF THE INVENTION

The present invention is directed to antibodies capable of reacting with specificity to CD44 variants which contain the amino acid sequence encoded by exon v6. Among such variants would be all of those containing domain 3.

The present invention is also directed to a method of detecting pathological conditions by determining whether specific variant forms of CD44 are being expressed in cells. In a preferred embodiment, the loss of expression of cell surface CD44v6 is used to detect the malignant transformation of cells as well as the metastatic potential of those cells that lo have undergone malignant transformation. In a still more preferred embodiment, the reagent used to detect the loss of CD44v6 is a monoclonal antibody.

In another preferred embodiment, the invention is directed to the detection of inflammatory states in individuals by measuring CD44v6 in serum samples. Inflammatory diseases that can be detected using this method include rheumatoid arthritis and inflammatory bowel diseases.

DETAILED DESCRIPTION OF THE INVENTION

Definitions

The following definitions are provided:

1. CD44:CD44 is a multifunctional glycoprotein found on the surface of a number of cells and involved in adhesion-dependent processes. The protein occurs in several different forms which are termed "isoforms." A 90 kD form is referred to as the standard or lymphocyte form. There is also an 150 kD isoform which is found in epithelial cells.

2. CD44 variants: All forms of CD44 other than the 90 kD lymphocyte form are called variants. Variants contain the 90 kD lymphocyte CD44 protein but have additional amino acid sequence elements ("domains") as well. The domains making up the CD44 variants are the result of the differential splicing of at least 10 exons comprising the CD44 gene.

3. CD44v6 : Those variants of CD44 which contain within their primary structure the amino acid sequence encoded by exon 6 are termed "CD44v6."

4. Exon v6: Exon v6 is defined as nucleotides 1140–1267 of the CD44 gene of humans (Arch, R. et al., *Science* 257:682–685 (1992); Hoffman, M. et al., *Cancer Res.* 51:5292–5297 (1991)). The sequence of exon v6 is shown in FIG. 11.

5. Hermes 3: Hermes 3 is a monoclonal antibody recognizing a site on the 90 kD lymphocyte protein present in all forms of CD44.

6. Var3.1. Var3.1is a monoclonal antibody by a hybridoma cell line deposited with the International Depositary Authority DSM Deutsche Sammlung Von Mikroorganismen Und Zellkulturen GmbH at the address Mascheroder Weg 1 B, D-38124 Braunschweig, Germany. The deposit was made on Jun. 4, 1993 and was given the accession number DSM ACC2131. The antibody is specific for those forms of CD44 containing the amino acid sequence encoded by exon v6.

7. The abbreviation "PBL" stands for "peripheral blood lymphocytes"; mab stands for "monoclonal antibody"; FCS stands for "fetal calf serum"; and PBS stands for "phosphate buffered saline".

8. Inflammatory diseases: Inflamatory diseases are those diseases characterized by the cellular and histologic reactions associated with inflammation. The typical signs of inflammation are redness; a localized feeling of warmth; swelling; pain; and sometimes, a loss of normal function.

9. Metastatic Potential: Metastatic potential is defined as the tendency of neoplastically transformed cells to migrate from one part of the body to another. Typically, metastatic potential will be expressed as the percentage of total tumor cells colonizing new sites.

10. Malignant transformation: Malignant transformation is the change of normal cells to cancerous cells. The main characteristics which indicate that a malignant transformation has occurred are uncontrolled cellular proliferation and a loss of differentiated function.

Monoclonal Antibody Specific for the Amino Acid Sequence Encoded by Exon v6

The present invention is directed to monoclonal antibodies which react specifically with those forms of CD44 that contain within their primary structure the amino acid sequence element encoded by exon v6 (FIG. 11). Methods for producing monoclonal antibodies specific for particular antigens are well known in the art and a procedure adapted to the production of monoclonal antibodies to the peptide encoded by CD44 exon v6 is described below in Example I. The antibody produced in the Example was given the designation Var3.1 and the hybridoma cell line producing this antibody was deposited with the International Depositary Authority DSM Deutsche Sammlung Von Mikroorganismen Und Zellkulturen GmbH at the address Mascheroder Weg 1 B, D-38124 Braunschweig, Germany. The deposit was made on Jun. 4, 1993 and was given the accession number DSM A.C.C. 2131.

The invention contemplates a variety of uses of exon v6-specific antibodies in general and of Var3.1 in particular. In all cases, detection of antibody-antigen complexes can be accomplished either using a labeled second antibody, i.e. an antibody recognizing an immunoglobulin chain present in the antibody binding to the exon v6-encoded antigen, or by labeling the first antibody directly. Examples of labels which are typically used for such purposes include radioactive labels (e.g. $^{125}I$, $^{131}I$, $^{14}C$ or $^{3}H$); biotin; fluorescent labels (such as fluorescein, rhodamine or phycoerythrin) or enzymes (such as horseradish peroxidase, alkaline phosphatase or urease). Techniques for incorporating such labels into antibodies and for detecting labeled antibody-antigen complexes are well known in the art (see e.g. Hood et al. *Immunology*, 2nd edition, chapter 3 (1984)).

Monoclonal antibody Var3.1 is the first mAb reported that can discriminate human CD44v6 from those forms of CD44 that do not possess exon 6. The use of this and similarly directed monoclonal antibodies for research purposes is encompassed by the present invention and is illustrated below. The result of studies examining the expression of CD44v6 in normal and diseased states led to the conclusion that there is a correlation between the expression of this antigen and malignant transformation, the metastatic potential of transformed cells and the presence of inflammatory diseases in people.

CD44v6 Expression in Normal Cells

Studies using Var3.1 to examine antigen expression in normal cells are described in detail in Example I and are summarized below. These studies illustrate the way in which this antibody can be used for research purposes. Moreover, the results from normal samples, when compared to the results obtained in later studies using malignantly transformed samples or samples obtained from patients with inflammatory diseases shows that the expression of the CD44v6 antigen can be used for diagnostic purposes.

CD44v6 was found to be present in different types of epithelial cells, dendritic cells and in the endothelial cells of blood vessels. Most abundant expression was seen in squamous epithelial cells, where the Var3.1 epitope appeared to be concentrated on the superficial side of the cells. Comparison of the expression patterns between mAb Var3.1 and Hermes-3, an antibody which binds to the constant part of the CD44 molecule, revealed several interesting features (summarized in Table I).

At surface epithelia of tonsils, the reactivity of Var3.1 and Hermes-3 was different. Var3.1 stained the cells in the mid and upper layers of the epithelium most intensely, whereas the basal layers displayed greatest reactivity with mAb Hermes-3.

Connective tissue components were strongly reactive with Hermes-3 but did not stain with mAb Var3.1. High endothelium of blood vessels, on the other hand, was Var3.1-positive, but Hermes-3-negative.

CD44v6 was not present on lymphoid cells of secondary lymphatic organs or on the surface of peripheral blood lymphocytes. All these leukocyte populations, however, stained brightly with mAb Hermes-3. Thus, the expression of exon 6 is restricted to a few specialized cell types, whereas Hermes-3 epitope is present on a wide variety of cells.

In contrast to the expression on the surface of epithelial cells in vivo, peripheral blood leukocytes and several epithelial cell lines only expressed CD44v6 intracellularly. It apparently distributed both as a membrane-associated form and diffusely in the cytoplasm. The acetone treatment per se (used for permeabilization) was not necessary for the accessibility of the Var3.1 epitope to mAb, since mAb Var3.1 stainings produced identical reaction patterns on acetone-fixed and non-fixed cryostat sections of tonsil. Therefore, acetone does not unmask the Var3.1 epitope by dissolving some lipid constituents of the cell membrane.

A considerable amount of CD44v6 was in a NP-40-insoluble form, and thus, is most probably linked to cytoskeletal proteins. The cytoplasmic tail of the standard CD44 is known to be associated with ankyrin, which links transmembrane proteins to actin and fodrin in mouse T-lymphoma cells (Kalomiris, E. L. et al., *J. Cell Biol.* 106:319–327 (1988)). CD44 also co-localizes with vimentin in WI-38 and with actin in 3T3 cells (Carter, W. G. et al., *J. Biol. Chem.* 263:4193–4201 (1988); Lacy, B. E. et al., *J. Cell. Biol.* 105:1395–1404 (1987)). Furthermore, A3D7 and Hermes-1 (other anti-CD44 antibodies against the constant part of CD44) reactive material has been shown to exist in an NP-40 insoluble form in human T cells (Geppert, T. D. et al., *J. Immunol.* 146:3298–3305 (1991)). Our results suggest that CD44v6 can, at least partly, account for these previously described detergent insoluble forms of CD44.

CD44v6 Expression Can be Used in the Diagnosis of Malignant Transformation and in Assessing the Metastatic Potential of Tumor Cells The expression of CD44v6 was not altered in benign epithelial neoplasms. In contrast, malignant transformation was associated with the down-regulation of CD44v6. Moreover, the variant CD44v6 was practically absent from the metastatic cells. In contrast, the majority of malignancies remained Hermes-3 positive. These observations held true in the material of 37 epithelial tumors studied (see Example I).

The results suggest that exon v6 is not responsible for the invasiveness or metastasis of epithelial squamous carcinomas. Rather, its expression seems to be associated with the regulated, normal differentiation and proliferation of epithelial cells. Its expression is silenced during malignant transformation.

The above results are in agreement with results reported in the literature. In a recent study on the effects of standard and epithelial CD44 isoforms on tumor growth in an in vivo model, the standard 80–90 kD form, but not the epithelial form, enhanced tumor invasiveness and metastatic activity (Sy, M. S. et al., *J. Exp. Med.* 174:85–866 (1991)). In studies of non-Hodgkin lymphomas, surface expression of Hermes-3 correlated positively to the prevalence of metastasis (Horst, E. et at., *Leukemia* 4:595–599 (1990); Jalkanen, S. et al., *J. Clin. Invest.* 87:1835–1840 (1991)). Since we were unable to detect exon v6 on the surface of any leukocyte subset or line, standard form is the most likely candidate in mediating the metastatic behavior of non-Hodgkin lymphomas as well.

Although the loss of CD44v6 expression is correlated with malignant transformation and increased metastatic potential in epithelial cells, other changes may take place when cells of a different origin undergo transformation. For example, Günthert et al. found that expression of the variant form of CD44 in a rat carcinoma cell line resulted in the acquisition of metastatic properties (Günthert, U. et al., *Cell* 65:13–24 (1991)). The expression of exon v6 was implicated as having a central role in this process.

It appears most likely, that the different cellular origin of the malignant material accounts for the differences observed. The studies on Var3.1 described above used carcinomas derived from human keratinocytes, whereas two adenocarcinoma cell lines with their derivatives/variants were studied in the rat model (Günthert, U. et al., *Cell* 65:13–24 (1991)). Preliminary studies in human samples using Var3.1 on adenocarcinoma specimens indicate that, in certain cases, exon v6 is up-regulated during malignant transformation. In a recent paper, it was reported that several alternatively-spliced large molecular weight variants were overproduced in malignant tumors of breast and colonic tissue in man when analyzed by PCR and hybridization (Matsumura, Y. et al., *Lancet* 340:1053–1058 (1992)). Thus, the role of CD44 in tumor metastasis may be dependent on the species, type of carcinoma or host microenvironments.

In terms of the invention as claimed herein, the results indicate that monoclonal antibodies specific for an epitope encoded by exon v6 can be used to detect malignant transformation and metastatic potential. In the case of malignant transformation, samples of the tissue suspected of being malignant would be obtained using standard biopsy techniques. Monoclonal antibody would then be used to compare the amount of CD44v6 present in the biopsy samples with the amount present in reference samples taken from the same type of tissue but from individuals known to be normal. The exact procedure used for the assay could follow the immunohistochemical procedures described in Example I or could take the form of other standard diagnostic immunoassays. In tissues of epithelial origin, malignant transformation should be accompanied by a loss of exon v6 antigen relative to normal tissue.

Assays performed for the purpose of evaluating the metastatic potential of cells would be similar to those for detecting malignant transformation except that comparison would be between a biopsy sample and cells known to be malignantly transformed but non-metastatic. Again, sample and reference tissue should be matched according to organ type, e.g. liver samples should be compared with references of liver origin. In the case of tissues of epithelial origin, increased metastatic potential should be inversely correlated with the presence of the CD44v6 antigen.

CD44 v6 Expression Can be Used in the Diagnosis of Inflammatory Diseases

Serum samples from normal individuals and from individuals suffering from chronic inflammatory diseases (either rheumatoid arthritis or inflammatory bowel disease) were collected and examined for the presence of CD44v6 antigen using the Var3.1 antibody. Assays performed using the dot blot procedure described in Example I (under the Material and Methods section) indicated that samples from patients with inflammatory diseases showed strong reactivity with the antibody whereas samples obtained from normal individuals showed no or weak reactivity.

These results indicate that the CD44v6 epitope can be used for the diagnosis of inflammatory diseases. Serum samples from patients suspected of having inflammatory bowel disease would be compared to serum samples from normal individuals. The exact procedure could follow the dot blot procedure set forth in Example I or any other commonly used immunoassay procedure. The presence of inflammatory disease would be detected as an increase in antibody reactivity in the collected samples relative to the normal reference samples.

Having now generally described this invention, the same will be further described by reference to certain specific examples which are provided herein purposes of illustration only and are not intended to be limiting unless otherwise specified.

EXAMPLE I

Materials and Methods

Production of mAb against human exon v6 of variant CD44

A synthetic peptide representing a 16 amino acid sequence from the exon v6 of the human variant CD44 (STTEETATQKEQWFGN [SEQ ID NO: 10], Hoffman, M. et al., *Cancer Res.* 51:5292–5297 (1991); an additional C-terminal cysteine was included for coupling purposes) was prepared using an automated peptide synthesizer (Model 431 A, Applied Biosystems, CA). Purification of the peptide was carried out with a preparative HPLC (Applied Biosystems) using a reverse phase column and its purity was confirmed by an analytical HPLC. The peptide was also independently sequenced (Model 477A equipped with an online PTH amino acid analyzer 120A, Applied Biosystems) and analyzed with desorption time-off-flight mass analyzer (BioIon $^{TM20}$ Biopolymer Mass Analyzer, Applied Biosystems) and found to be correct. One hundred microgram peptide in incomplete Freund's adjuvant was injected into the footpads of specific pathogen free Balb/c mice three times at one week intervals. After sacrificing lymphocytes from popliteal lymph nodes were isolated and fused with NS-1 myeloma cells using standard procedures. Hybridoma supernatants were tested in ELISA (see below) using the synthetic peptide as an antigen and a positive hybridoma (designated Var3.1) was subcloned twice by limiting dilution. The isotype of mAb Var3.1 was Ig $G_1$.

Production of anti-CD44 mAbs of Hermes-series has been described earlier (Jalkanen, S. T. et al., *J. Cell. Biol.* 105:983–990 (1987)). Hermes-3 recognizes an epitope in the proximal extracellular part of the constant region of CD44 (Goldstein, A. L. et at., *Cell* 56:1063–1072 (1989)). 3G6, a mouse mAb against chicken T cells, was used as a negative control. All antibodies were used as serum-free supernatants or as $(NH_4)_2SO_4$ precipitated concentrates.

ELISA

The synthetic peptide from the exon v6 and a control peptide (FIG. 1.) were absorbed to the bottom of microtiter wells (Dynatech Laboratories, Alexandria, Va.) overnight at 37° C. (10 µg well). After washings, the remaining binding sites were blocked with 1% gelatin, and after washings the primary antibodies were added for 2h Alkaline phosphatase-conjugated goat anti-mouse IgG and 1 gM (Tago, Burlingame, Calif.) was used as the second stage antibody, and p-nitrophenylphosphate as the substrate. Absorbances were read in Multiscan (Labsystems, Helsinki, Finland) at 405 nm.

Construction and analysis of pGEX-2T-fusion proteins containing exon v6 of human variant CD44

Exon v6 containing form of CD44 was amplified from HaCaT cells by reverse transcriptase polymerase chain reaction (PCR) and cloned into pGEX-2T vector (Smith, D. B. et al., Gene 67:31–40 (1988)) for fusion protein production. HaCaT RNA was isolated by the guanidine isothiocyanate phenol extraction method. First strand cDNA synthesis was carried out using 1.5 µg total RNA, oligo(dT) primer and M-MLV reverse transcriptase according to the instructions of the manufacturer (Perkin Elmer Cetus, Norwalk, Conn.). Because HaCaT cells have several forms of CD44 (unpublished PCR data, K. G-V., M. S., S. J.), existence of v6 in the PCR product was ensured by using two sets of primers in two separate PCR amplification reactions as schematically illustrated in FIG. 2A. In one reaction (Ia), primers A and B were used and in the other reaction (Ib), primers C and D were employed. Thereafter, the products were combined in a reaction using primers E and F which contained Barnill and EcoR1 tails, respectively. The presence of exon v6 in the 0.95 kb PCR product was confirmed by dot blot hybridization with the P32-labeled probe G.

The 0.95 kb fragment (including exons v6–10) was isolated from 1.5% agarose gel, digested with Barnill and Eco R1 and ligated using T4 ligase (Stratagene) into pGEX-2T expression vector (Sambrook, J. et al., "Molecular Cloning: A Laboratory Manual", Cold Spring Habor Laboratory Press (1989); Smith, D. B. et al., Gene 67:31–40 (1988)). Hereafter, the plasmid pGEX-2T with the 0.95 kb v6 containing insert is called pGEX-2T-Var. Bacteria (E. coli DH5a strain) were transformed with pGEX-2T-Var using $CaCl_2$ method. Production of fusion protein was induced with isopropyl β-D-thiogalactopyranoside (IPTG), after which bacteria were pelleted and lysed in Laemmli's sample buffer containing 2% SDS. Samples from whole cell lysates of pGEX-2T-Var and pGEX-2T (control) transformants were run on a 5–12.5% SDS-PAGE. After electrophoresis, the proteins were transferred onto nitrocellulose membranes (Schlieicher-Schuell, Dassel, Germany) by blotting 1.5 h at 1A in a Transphor apparatus (Hoefer, San Francisco, Calif.). The membranes were then soaked for 48h in PBS containing 0.1% Tween-20 and 1% non-fat milk powder. After washings in PBS, membranes were cut into strips and incubated overnight with primary antibodies. After washing, a 3 h incubation in PBS containing peroxidase-conjugated rabbit anti-mouse Ig (Dakopatt A/S, Glostrup, Denmark) was performed. After extensive washing, the membranes were developed in PBS containing 16% methanol, 0.5 mg/ml 4-chloro-1-naphthol (Sigma) and 0.01% hydrogen peroxide. Same amount of samples were also run on parallel gels which were subsequently fixed in 40% methanol and 10% acetic acid and stained with Coomassie Brilliant blue.

Purification of CD44 and Western blotting

PBL from leukopheresis samples of patients suffering from rheumatoid arthritis were used for CD44 antigen isolation as previously described (Jalkanen, S. et al., J. Cell. Biol. 116:817–825 (1992)). Briefly, lymphocytes (25 ml packed cells) were lysed in lysis buffer (1% NP-40, 0.15 M NaCl, 0.01 M Tris, 1.5 mM $MgCl_2$ and 1 mM PMSF, pH 7.0). The clarified lysate was applied first to a Sepharose CL-4B (Pharmacia, Uppsala, Sweden) column and then sequentially to three CnBr-activated Sepharose-4B (Pharmacia) columns derivatized with normal mouse serum, with irrelevant mAb and with Hermes-3 mAb (5 mg/ml, 3 ml column volume). The column was washed extensively with the lysis buffer. Thereafter, the material bound to the Hermes-3 column was eluted with 50 mM triethylamine and lyophilized. Isolated CD44 was subjected to SDS-PAGE and blotting as described above for fusion proteins with the exception that membranes were blocked in 0.1% Tween-20 for 3h and 5% AB-serum (Finnish Red Cross, Helsinki, Finland) was added with the second-stage antibody.

Immunohistochemistry and Immunoelectronmicroscopy

Tissue distribution of the different forms of CD44 was determined using immunoperoxidase staining. Surgical and skin punch biopsy specimens were snap frozen in liquid nitrogen. Five µm frozen sections were cut, air-dried and acetone fixed. Sections were overlaid with mAb supernatants and incubated for 30 min at room temperature in a humidified chamber. After two washings in PBS, peroxidase-conjugated rabbit anti-mouse Ig in PBS containing 5% AB-serum was added. Finally, the reaction was developed by adding 3,3-diaminobenzidine (Polysciences, Inc., Warrington, Pa.) in PBS containing 0.03% hydrogen peroxide for 3 min. After staining, the sections were counterstained in hematoxylin (Sigma Chemicals, St. Louis, Mo.), dehydrated, cleared in xylene and permanently mounted in DePex (BDH Limited, Pool, Dorset, England).

For immunoelectronmicroscopy, samples from human tonsils were snap-frozen in freon 22 chilled with liquid nitrogen. About 15 µm frozen sections were stained either immediately or after short fixation in −20° C. acetone. The immunoperoxidase staining was performed as described above. The reactions were followed by fixation in phosphate buffered 2% glutaraldehyde. Thereafter, a representative section was examined light microscopically, and an appropriate area was selected. The corresponding area in parallel sections was trimmed, sections were postfixed in phosphate buffered 2% osmium tetroxide, dehydrated and embedded in epon at the open end of an inverted BEEM capsule. Alternatively, gold labeling was done by sequential incubations with mAb Var3.1, biotinylated horse anti-mouse Ig (Vector laboratories, Burlingame, Calif.), and aggregated streptavidin-gold solution (Zymed, San Francisco, Calif.). Slides were processed similarly as described for immunoperoxidase reaction, except that silver intensification was used for visualization of the reaction product, and osmium tetroxide fixation was omitted. Thin sections were double-stained with uranyl acetate and lead citrate and then examined in a JEM 100 electron microscope. Slides processed without the primary or secondary antibody, with and without the double staining served as controls.

Cells and Cell Lines

Human PBL were isolated from healthy adult volunteers using Ficoll-gradient (Ficoll-Hypaque, Pharmacia) centrifugation. PBL were used fresh or, to obtain activated blast cells, stimulated with combination of 10 μg/ml PHA (phytohemagglutinin) and 1:100 PWM (Gibco, Grand Island, N.Y.) for 3 days at 37° C. in RPMI 1640 (Gibco) supplemented with 10% FCS, glutamine, Hepes, sodium pyruvate, penicillin and streptomycin. Human cell lines HeLa (epithelioid carcinoma), KG-1, KG-1a, K-562, U937 (leukemic cells), and A549 (lung carcinoma) were obtained from American Type Culture Collection (Rockville, Md.). U1690 (human lung carcinoma cell line) was a kind gift from Dr. H. Hirvonen (Department of Medical Biochemistry, Turku University, Finland) and HaCaT, a spontaneously immortalized, nontumorigenic keratinocyte line, was a kind gift from Prof. N. E. Fusenig (German Cancer Research Center, Heidelberg, Germany). All cell lines were cultured in Dulbecco's modified minimal essential medium (Gibco) supplemented with 10% human AB-serum, 10 mM Hepes and antibiotics and adherent cells passaged using trypsin-EDTA (Boehringer-Manheim, Germany).

Immunofluorescence Staining

Blood cells and adherent cell lines (detached with 5 mM EDTA in $Ca^{2+}$, $Mg^{2+}$-free HESS) were stained in suspension. Cells were stained unfixed or after fixation and permeabilization (1% formaldehyde in PBS (10 rain) followed by −20° C. acetone (5 min) followed by two washings in PBS). Cells were incubated with primary antibodies for 20 min at 4° C. and washed twice in PBS containing 5% FCS and 1 mM sodium azide. Next, FITC-conjugated sheep anti-mouse IgG (Sigma) in PBS containing 5% human AB-serum was added for 20 min. Thereafter, the cells were washed twice and fixed in PBS containing 1% formaldehyde. Analyses were done using a FACScan cytometer (Becton Dickinson, Mountain View, Calif.). For immunofluorescence microscopy cells were spun on microscopic slides with Cytospin 2 cytocentrifuge (Shandon Southern, Surrey, England) and mounted in glycerol containing 10% PBS. Alternatively, adherent cells were grown on glass coverslips, and processed without detachment for immunofluorescence microscopy as described above.

When studying the detergent resistance of Var3.1 and Hermes-3 epitopes, HaCaT cells grown on glass slides and cytocentrifuge preparations of PBL were used. Cells were first fixed and permeabilized as described above. Thereafter, cells were incubated in PBS with or without 0.5% NP-40 for 5 min at 4° C. and washed twice. Next, the cells were stained for immunofluorescence as described above, and analyzed using fluorescence microscopy. Similar results were obtained, when the cells were first stained and thereafter treated with the detergent.

PCR Amplification of Lymphocyte v6

Total RNA was isolated from PBL obtained from blood donors and from HaCaT cells using guanidine isothiocyanate method and reverse transcribed to cDNA. To study the presence of exon v6 containing mRNA in these cells, primers B and C (FIG. 2A) were used for PCR. The PCR products were separated in 1.5% agarose gel, blotted onto nylon membranes (Zeta-Probe, BioRad), hybridized to a $P^{32}$-labeled oligonucleotide probe from exon v6 (probe G in FIG. 2A) according to standard procedures for Southern blotting (Sambrook, J. et al., "Molecular Cloning: A Laboratory Manual", Cold Spring Habor Laboratory Press (1989)). As controls, parallel reactions were performed that contained all the reagents except reverse transcriptase.

Dot Blot Assay

Serial dilutions of serum samples or BSA (50 μg/well as control) were transferred onto a nitrocellulose membrane (Schleicher-Schuell) using a dot blot apparatus. The membrane was blocked in 1%non-fat milk for 2h at room temperature and then washed twice in PBS. Thereafter, the membrane was cut into strips and the strips were stained as described above for Western blottings.

Results

Establishment of the Human Variant Exon 6-Specific Monoclonal Antibody

Exon v6 has been reported to play a crucial role in the development of metastatic deposits of rat adenocarcinoma cells (Günthert, U. et al., *Cell* 65:13–24 (1991)). To study the expression of CD44v6 in man, mAbs against a synthetic polypeptide from the exon v6 were produced. The hybridomas were screened by ELISA. Supernatant from one hybridoma specifically recognized the peptide used for immunization (FIG. 1). This exon v6 specific mAb (designated mAb Var3.1) was selected for further studies after subcloning.

Figures 2B, 2C:
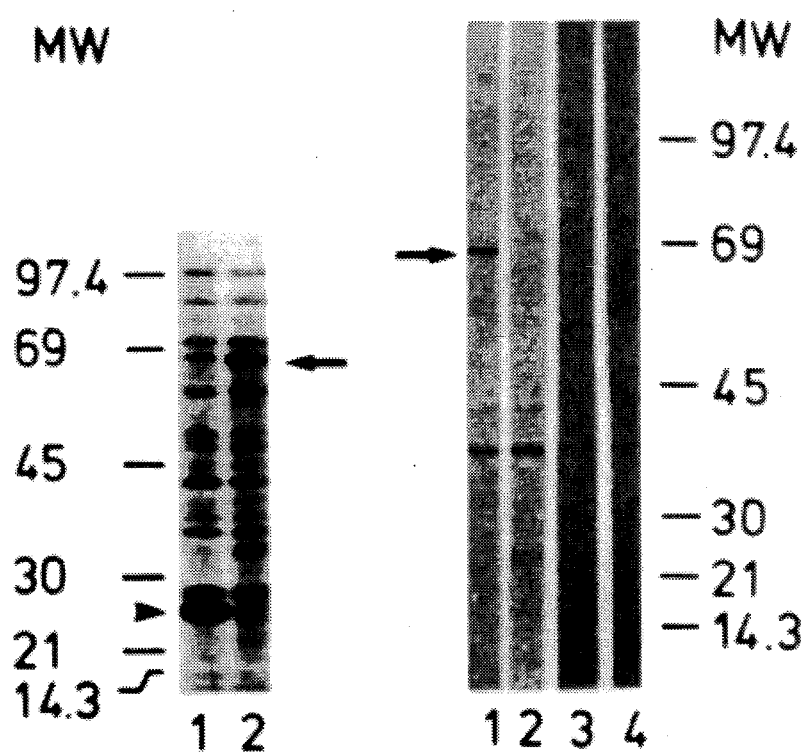

The specificity of mAb Var3.1 was demonstrated by showing that it reacted with a recombinant protein containing human v6. Since HaCaT cells express several forms of CD44, inclusion of v6 was ensured by making the PCR reaction in two steps (FIG. 2A). First, variant CD44 was produced in two reactions in which the primer C was from exon v6 (and both B and C from the sequence that was formerly called domain 3, Hoffman, M. et al., *Cancer Res.* 51:5292–5297 (1991)) and thus determined the specificity of the reaction. Next, these two PCR products were joined by using primers from the constant part of CD44. The 0.95 kb PCR product was then cloned into pGEX-2T expression vector and E. coli were transformed with the construct. After IPTG-induction, proteins from whole bacterial lysates were separated in SDS-PAGE and subjected to Coomassie staining (FIG. 2B). Bacteria transformed with pGEX-2T-Var produced an IPTG-inducible ~60 kD molecule, while pGEX-2T encoded for an inducible ~28 kD molecule. Next, whole cell lysates of transformed bacteria were subjected to SDS-PAGE and Western blotting (FIG. 2C). It was found that mAb Var3.1 reacted with the ~60 kD fusion protein but not with the product of the parent vector alone. A negative control mAb failed to stain the ~60 kD molecule. Together, the results of ELISA and fusion protein assays unambiguously show that mAb Var3.1 recognizes v6 of CD44 in man.

Immunoblotting analyses of Hermes-3 purified CD44 antigen from leukopheresis samples revealed that under nonreducing conditions mAb Var3.1 recognized two major bands (~220 and 300 kD), and one faint bigger band (FIG. 3). This experiment shows that mAb Var3.1 recognizes an epitope of purified CD44. MAb Hermes-3 stained proteins of very variable sizes (70–300 kD) from the purified CD44 material (FIG. 3).

Expression of CD44v6 in Normal Tissues

Figure 4A:
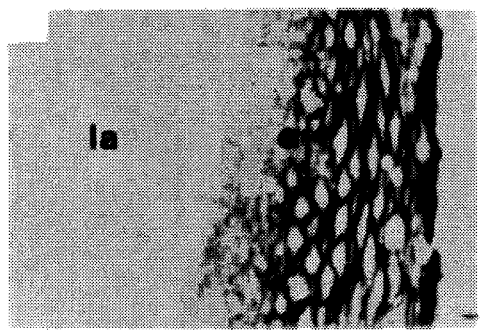
Figure 4B:
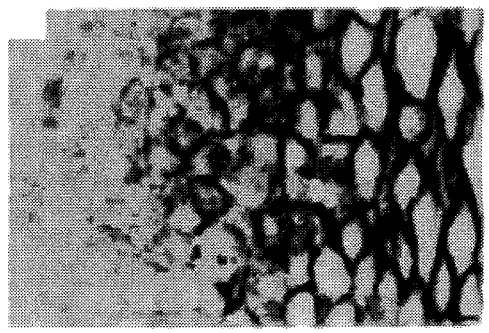
Figure 4C:
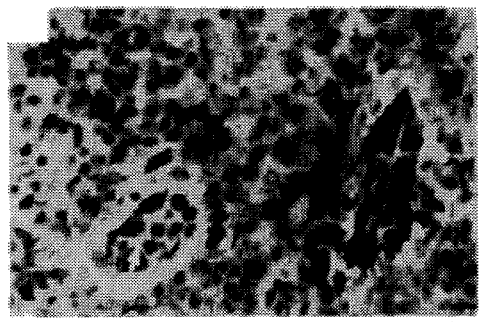
Figure 4D:
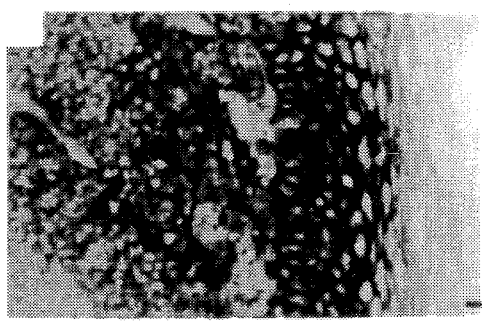
Figure 4E:
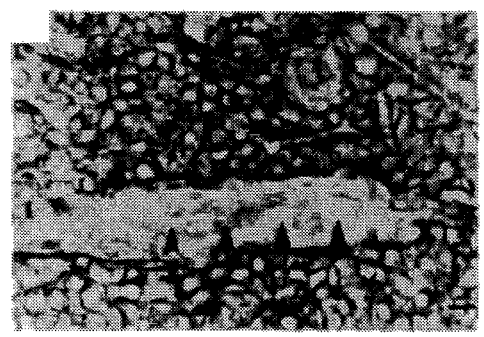

Immunoperoxidase staining of frozen sections from normal human tissues was performed to study the tissue distribution of CD44v6. In the tonsil, surface epithelium intensely stained with mAb Var3.1 (FIG. 4A and B). Reactivity was particularly strong in the mid and upper layers of stratified squamous epithelium (upper stratum spinosum and stratum granulosum), while cells in the basal layers exhibited fainter staining. Reticulated crypt epithelium also stained positively with mAb Var3.1. Tonsillar lymphocytes were practically non-reactive with mAb Var3.1, as were connective tissue components (FIG. 4A). In germinal centers, mAb Var3.1 faintly reacted with cells of dendritic morphology, Luminal surface of some blood vessels, including high endothelial venules, also stained with mAb Var3.1 (FIG. 4C). In comparison, expression of the Hermes-3 epitope on tonsillar surface epithelium was most pronounced basally and notably less was seen in upper layers (FIG. 4D). MAb Hermes-3 intensely reacted with practically all lymphocytes outside the germinal centers, and fibroblasts were strongly positive in the septae. On the other hand, endothelial lining of most vessels and all high endothelial venules were Hermes-3 negative (FIG. 4E).

Figure 5A:
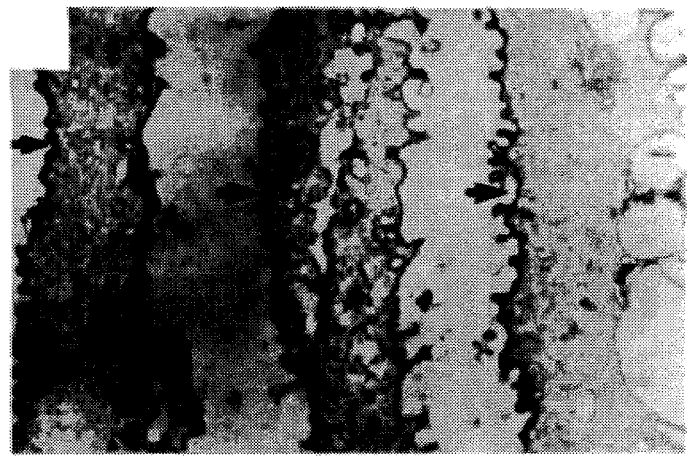
Figure 5B:
Figure 6A:
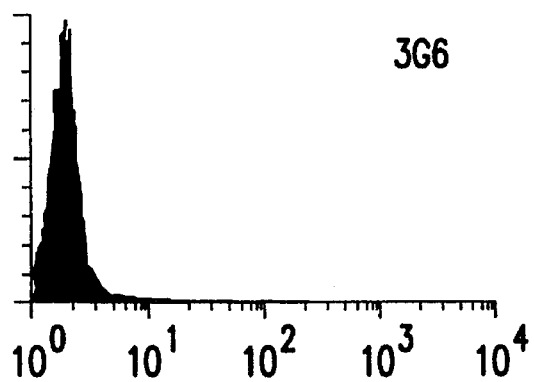
Figure 6B:
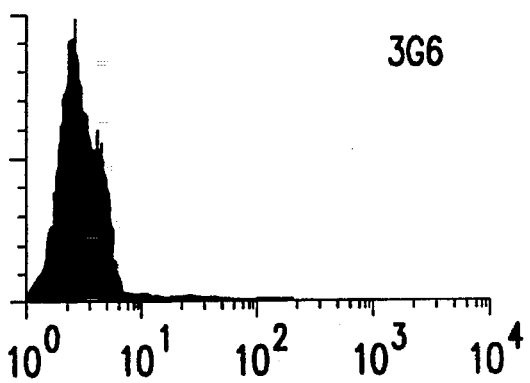
Figure 6C:
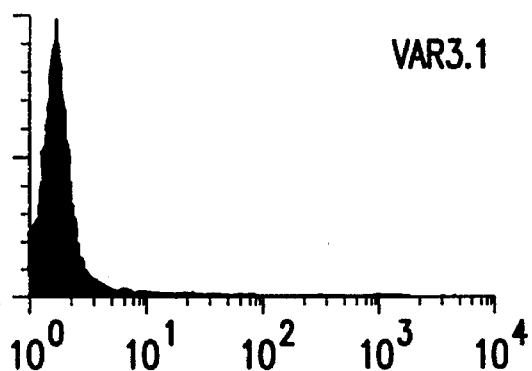
Figure 6D:
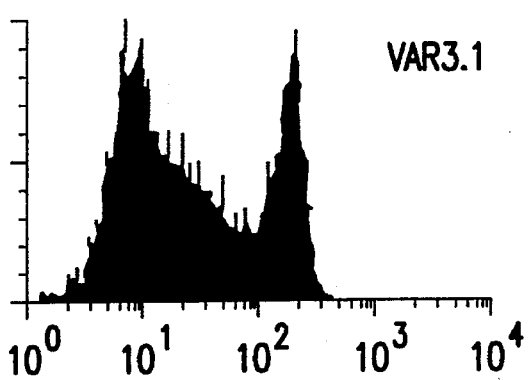
Figure 6E:
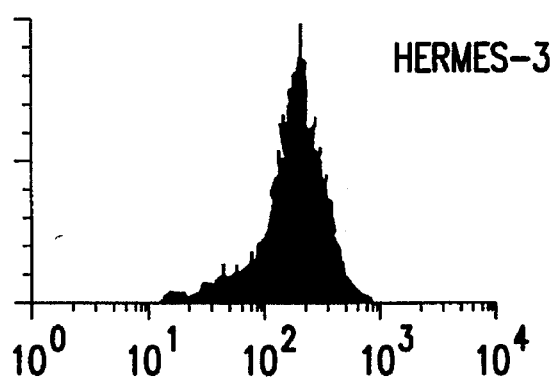
Figure 6F:
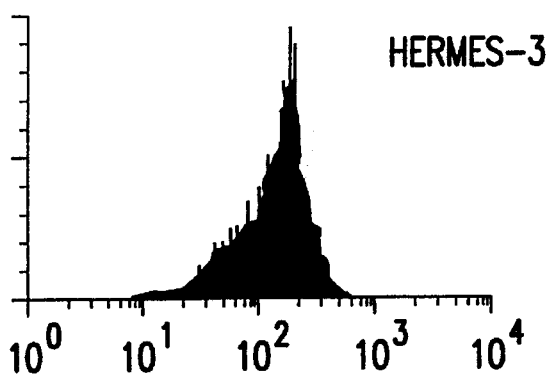
Figure 6G:
Figure 6H:
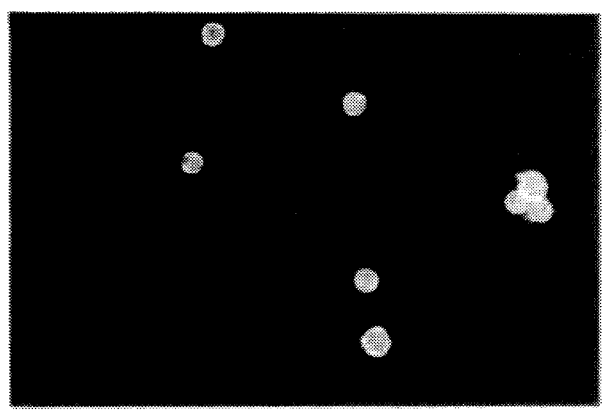
Figure 6I:
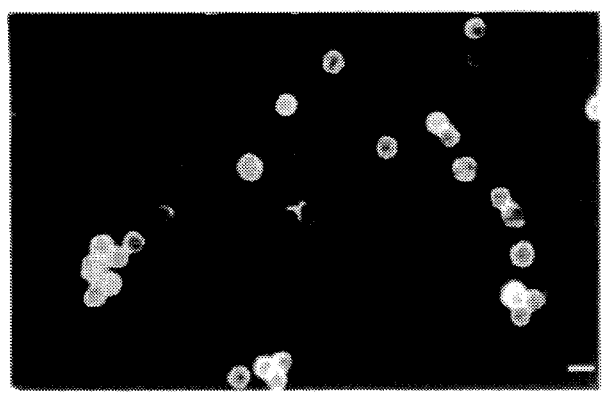

In electron microscopy the plasma membrane of the superficial squamous cells stained homogeneously dark in the peroxidase preparations, and the staining was usually more intense on the superficial side of the cell (FIG. 5A). In gold preparations the particles were localized along the surface of the superficial squamous cells (FIG. 5B).

TABLE I

Cell and tissue distribution of VAR3.1 and Hermes-3 epitopes of CD44

|  | Var3.1 | Hermes-3 |
|---|---|---|
| Blood cells (surface) |  |  |
| PBL | − | ++ |
| granulocytes | − | ++ |
| monocytes | − | ++ |
| Tonsil |  |  |
| lymphocytes | − | ++ |
| dendritic-like cells in germinal centers | + | + |
| HEV | + | − |
| surface epithelium | ++ | ++ |
| Skin |  |  |
| stratum basale | + | ++ |
| stratum spinosum | + | ++ |
| stratum granulosum | + | + |
| dermal fibroblasts | − | + |
| hair follicles | ++ | ++ |
| sweat glands | + | ++ |
| Intestine |  |  |
| lymphoid cells | − | ++ |
| enterocytes | −/+ | ++ |
| smooth muscle | − | ++ |
| Brain |  |  |
| neurons | − | − |
| glial cells | − | ++ |

Blood cells were surface-stained for immunofluorescence and analyzed with FACS. Frozen sections of tissues were stained using immunoperoxidase staining. Intensity of staining was scored as follows: −: negative, −/+: weak, +: moderate, ++: strong. HEV = high endothelial venules.

Expression patterns obtained by mAbs Var3.1 and Hermes-3 were clearly distinct in several other tissues in addition to tonsil (Table I). In the skin, CD44v6 was preferentially localized in the upper layers of the epidermis, except in keratinized surface layer that was negative. In the dermis, fibroblasts and other stromal elements were negative, while hair follicles and sweat glands stained positively with mAb Var3.1. Expression of the Hermes-3 epitope in the epidermis was most prominent basally, and in the dermis, Hermes-3 epitope was abundantly present in fibroblasts. In the intestine, enterocytes and dendritic cells of Peyer's patches showed weak reactivity with mAb Var3.1, whereas CD44v6 was absent from other structures. MAb Hermes-3 stained enterocytes much more strongly, and the Hermes-3 epitope was also present in lymphoid, smooth muscle and connective tissue cells of the gut. CD44v6 was not present on neurons or glial cells of brain white or gray matter. Peripheral nerves also lacked this molecule. In contrast, glial cells of white matter were intensely positive with mAb Hermes-3.

Intracellular Localization of CD44v6 in Blood Leukocytes and Cell Lines

CD44v6 was absent from the surface of PBL, monocytes and granulocytes as determined by FACS-analysis (FIG. 6). PWM/PHA-induced immunoblasts and plasma cells did not express this form of CD44 either. However, when the cells were subjected to permeabilization prior to the immunofluorescence staining, majority of both unactivated and activated lymphocytes expressed Var3.1 epitope (FIG. 6). Number of positive cells ranged between 50 and 100% in different individuals. In fluorescence microscopy, positive reactivity was preferentially localized in the periphery of the cells, and fainter diffuse staining was detectable throughout the cytoplasm (FIG. 6B). Moreover, existence of CD44v6 in normal PBL was confirmed by showing the presence of v6 specific RNA in these cells (FIG. 7). In contrast to mAb Var3.1, the Hermes-3 epitope was abundantly expressed on surfaces of all human blood leukocyte subtypes as confirmed in FACS and immunofluorescence microscopy analyses (FIG. 6).

We also tested several cultured cell lines for mAb Var3.1positivity. Human keratinocyte (HaCaT), epithelial carcinoma (HeLa, U 1690, A549) and hematopoietic (KG-1, KG-1a, K562, U937) cell lines all lacked CD44v6 on their surface. However, all of them tested after permeabilization (HaCaT, HeLa, U1690) showed clear intracellular staining with mAb Var3.1. In contrast to CD44v6, all cell lines displayed Hermes-3 reactivity both on the cell surface and in the cytoplasm (data not shown).

Molecular Form and Detergent Solubility of CD44v6

Since CD44 is known to associate with cytoskeleton, we determined whether CD44v6 would also be linked to cytoskeletal proteins. Permeabilized HaCaT cells were incubated in PBS with or without 0.5% nonionic detergent NP-40 and stained for immunofluorescence (FIG. 8). Immunofluorescence microscopy showed that considerable amount of CD44v6 was in NPAO insoluble form. In contrast, significant amount of Hermes-3 containing form of CD44 disappeared during the NP-40 treatment. Similar results were obtained when PBL were analyzed (data not shown).

No molecular mass for CD44v6 was obtained from NP-40 lysates of HaCaT cells in Western blotting or in immunoprecipitations after labeling with $^{35}$S-Methionine, $^{35}$S-Cysteine, $^{35}$Sulphate and $^{14}$C-Glucosamine, probably due to the poor NP-40 solubility of CD44v6 in these cells. Moreover, mAb Var3.1 also appears to be a poorly precipitating antibody. However, in immunoblotting of SDS solubilized HaCaT cells, a faint −200 kD band was seen (data not shown).

Downregulation of CD44v6 in Human Neoplasms

The role of different CD44 forms in spread of malignancies is currently under dispute. Therefore, we stained 37 samples from benign (7 papillomas) and malignant (total 30:5 metastatic, 5 grade III, 10 grade II and 10 grade I head and neck squamous cell carcinomas) epidermal tumors for expression of CD44v6. These experiments showed that all epidermal cells in benign neoplasms stained with mAb Var3.1 like their normal counterparts in the neighboring healthy tissue. In contrast, expression of CD44v6 was down-regulated in all carcinoma samples in the malignant areas. In general, better differentiated carcinomas displayed more intense mAb Var3.1 reactivity than the more undifferentiated ones. As examples, staining patterns of a benign papilloma and a squamocellular carcinoma are shown in FIG. 9. All distant metastatic lesions of squamocellular carcinomas were practically negative with mAb Var3.1. In contrast, Hermes-3 brightly stained all benign and majority of the malignant cell types, including the metastatic deposits, in these specimens (FIG. 9).

CD44v6 Levels in Serum are Increased in Patients with Inflammatory Diseases

Dilution series from serum samples of normal subjects and from patients suffering from chronic inflammatory disorders were analyzed using the dot blot assay (FIG. 10).

Normal sera showed no positive reactivity with MAb Var3.1. In contrast, samples from chronically ill (rheumatoid arthritis or inflammatory bowel diseased) patients contained material that strongly stained with CD44v6 specific MAb. Hermes-3 reactive material was not detected using this method.

All references cited herein are fully incorporated by reference. Having now fully described the invention, it will be understood by those of skill in the art that the scope may be performed within a wide and equivalent range of conditions, parameters and the like, without affecting the spirit or scope of the invention or any embodiment thereof.

What is claimed is:

1. A monoclonal antibody which binds to a peptide having the amino acid sequence STTEETATQKEQWFGN (SEQ ID No: 10) and to human CD44v6, but does not bind to the 90 kilodalton standard lymphocyte form of human CD44.

2. The monoclonal antibody of claim 1, wherein said monoclonal antibody is Var3.1, and wherein said monoclonal antibody is the antibody produced by the hybridoma DSM ACC2131, deposited with the International Depositary Authority DSM Deutsche Sammlung Von Mikroorganismen Und Zellkulturen GmbH at the address Mascheroder Weg 1 B, D-3300 Braunschweig, Germany.

3. A method for detecting the presence of CD44v6 in tissues or cells comprising reacting the antibodies of either of claims 1 or 2 with said tissues or cells.

4. A method of screening for malignant transformation of cells in a human tissue sample, said method comprising:

a) obtaining said tissue sample to be assayed;

b) determining the levels of CD44v6 present in said tissue sample by reacting said tissue sample with said monoclonal antibody of either of claims 1 or 3;

c) comparing the results obtained in step b) with the results from similar reactions carded out using reference samples wherein said reference samples are of the same tissue type as said tissue sample but are known to be normal; and d) identifying said malignant transformation of said cells in said tissue by detecting a statistically significant difference between the CD44v6 levels in said tissue sample and the reference samples.

5. The method of claim 4 wherein the tissue sample is of epithelial origin and wherein malignant transformation is indicated by a statistically significant decrease in CD44v6 relative to reference samples.

6. A method for estimating the metastatic potential of malignant cells of human origin comprising:

a) obtaining a tumor sample to be assayed;

b) determining the level of CD44v6 present in said tumor sample by reacting said tumor sample with said monoclonal antibody of either of claims 1 or 2;

c) comparing the results obtained in step b) with the results from similar reactions carried out using reference samples wherein said reference samples are tumor cells of the same type as said tumor sample but are known to be nonmetastatic; and d) identifying tumors of high metastatic potential as those wherein the difference between the CD44v6 levels in the tumor sample and the reference sample is statistically significant.

7. The method of claim 6 wherein the tumor sample is of epithelial origin and wherein high metastatic potential is indicated by a statistically significant decrease in CD44v6 relative to reference samples.

8. A method for screening for inflammatory diseases in patients comprising:

a) obtaining a serum sample from said patient;

b) determining the amount of CD44v6 present by reacting the sample with a monoclonal antibody which binds specifically to a site encoded by exon v6 of human CD44 and which does not bind to the 90 kilodalton standard lymphocyte form of human CD44;

c) comparing the results obtained in step b) with the results from similar reactions performed using serum samples from normal individuals;

d) identifying those individuals with inflammatory diseases as those whose serum samples have a statistically significant increase in CD44v6 relative to the amount of CD44v6 present in the serum samples from normal individuals.

9. The method of claim 8, wherein the monoclonal antibody of step b) is a monoclonal antibody which binds to the amino acid sequence STTEETATQKEQWFGN (SEQ ID NO: 10) and to human CD44v6, but does not bind to the 90 kildalton standard lymphocyte form of human CD44.

10. The method of claim 9, wherein said monoclonal antibody is the monoclonal antibody produced by the hybridoma DSM ACC2131.

11. A method of preparing an antibody with specificity against human CD44v6, said method comprising immunizing with a peptide antigen having the sequence STTEETATQKEQWFGN (SEQ ID NO: 10) and collecting the antibodies induced by said antigen.

12. An isolated peptide of about 16 amino acid residues having the sequence STTEETATQKEQWFGN (SEQ ID NO: 10).

13. The method of any of claims 8, 9 or 10, wherein said inflammatory disease is rheumatoid arthritis or inflammatory bowel disease.

14. The method of any of claims 8, 9 or 10, wherein the amount of CD44v6 is determined by means of a dot blot assay.

\* \* \* \* \*